United States Patent [19]

Erner

[11] Patent Number: 4,931,472

[45] Date of Patent: Jun. 5, 1990

[54] FLUORINATED TRIETHYLENEDIAMINE AS AN OXYGEN TRANSPORT AGENT

[75] Inventor: William E. Erner, Burke, Va.

[73] Assignee: Biomed Technology, Inc., Burke, Va.

[21] Appl. No.: 776,805

[22] Filed: Sep. 17, 1985

[51] Int. Cl.$^5$ ............................................. A61K 31/13
[52] U.S. Cl. .................................... 514/661; 514/832
[58] Field of Search ................... 514/249, 832, 661; 544/351

[56] References Cited

U.S. PATENT DOCUMENTS

| | | | |
|---|---|---|---|
| 3,335,143 | 8/1967 | Erner | 544/351 |
| 3,911,138 | 10/1975 | Clark, Jr. | 514/756 |
| 3,962,439 | 6/1976 | Yokoyama et al. | 514/832 |
| 4,105,798 | 8/1978 | Moore et al. | 514/832 |
| 4,110,474 | 8/1978 | Lagow et al. | 514/832 |
| 4,187,252 | 2/1980 | Lagow et al. | 514/832 |
| 4,252,827 | 2/1981 | Yokoyama et al. | 514/784 |
| 4,423,061 | 12/1983 | Yokoyama et al. | 514/832 |
| 4,425,347 | 1/1984 | Yokoyama et al. | 514/832 |
| 4,562,183 | 12/1985 | Tatlow et al. | 514/832 |

*Primary Examiner*—Douglas W. Robinson
*Attorney, Agent, or Firm*—Burns, Doane, Swecker & Mathis

[57] ABSTRACT

Fluorinated triethylenediamine compounds such as perfluorotriethylenediamine and the novel compounds undecafluorotriethylenediamine and decafluorotriethylenediamine, prepared by indirect fluorination of triethylenediamine by passing triethylenediamine over, e.g., cobalt trifluoride ($CoF_3$), are useful as a material capable of carrying oxygen in an aqueous emulsion for lifesaving a patient suffering from massive hemorrhage and for preserving internal organs in transplantation. The compounds undergo rapid biological elimination due to their low molecular weight.

17 Claims, No Drawings

FLUORINATED TRIETHYLENEDIAMINE AS AN OXYGEN TRANSPORT AGENT

FIELD OF THE INVENTION

This invention relates to novel artificial blood compositions useful as infusion fluids or perfusion fluids. More especially, this invention relates to the discovery that highly fluorinated triethylenediamine compounds are useful as oxygen transport agents in artificial blood compositions. This invention also relates to emulsions containing these compounds. These compounds have excellent stability and rapid biological elimination. The present invention encompasses the preparation of these highly fluorinated triethylenediamine compounds.

BACKGROUND OF THE INVENTION

Natural whole blood is oftentimes in short supply. New methods for prolonged preservation of blood in the frozen state and improvements in storage in the liquid state have resulted in more efficient use of available blood in some areas, but the world-wide need for blood for transfusion still exceeds the supply. Since it is unlikely that there will be any appreciable increase in supply, the need for blood for transfusion must be satisfied in some manner other than natural blood or its derivatives. An artificial blood, available in unlimited quantities and free from infectious agents and antigens, would be an extremely valuable therapeutic agent.

A number of years ago, the oxygen-carrying capacity and lack of toxicity of perfluorinated liquids were reported. Emulsions of fluorocarbon liquids were used as artificial bloods. In brief, over nearly the last 20 years, considerable work has been accomplished in connection with the use of fluorocarbons and fluorocarbon emulsions as oxygen transfer agents and as artificial bloods. It is inevitable that artificial blood will be commercialized and used throughout the world because of the significant need for such oxygen transport agents and the advantages of such agents over natural blood.

The most prominent requirements of an artificial blood substitute are efficient oxygen and carbon dioxide transport, biological inertness, lower vapor pressure and dispersibility to form emulsions.

Several synthetic fluorocarbon compounds are known to be useful as blood substitutes. Such compounds are described in U.S. Pat. No. 3,911,138 (Clark, 1975), which describes emulsions that contain perfluorinated cyclic hydrocarbons, and U.S. Pat. Nos. 4,110,474 and U.S Pat. No. 4,187,252 (Lagow et al, 1978 and 1980), which describe emulsions that contain perfluorotetramethylpentane. U.S. Pat. No. 3,911,138 sets forth the various advantages and needs for artificial blood and may be referred to as further background of this invention. Continuing work is being done to create and identify other compounds which are suitable as blood substitutes, perfusion media, breathable liquids, and for other biological and chemical purposes. Such compounds are likely to have superior qualities regarding one or more relevant characteristics, which include: oxygen affinity and release, solubility or emulsifiability in various media, low toxicity, high shelf life, appropriate stability within the body, low retention within vital organs of the body, and low cost of manufacture.

Emulsions made from perfluorocyclo compounds have been found useful as blood substitutes because the cyclic fluorocarbon is transpired by the body through the skin and the lungs. However, in order for these emulsions to be preferred for biological use, they must be freshly prepared because they are not stable. In the emulsion, the particles making up the internal phase (dispersed phase) consist of globules of fluoro compounds which are immiscible with the aqueous external phase (dispersion medium). The stability of the internal phase in the fluorochemical emulsion is important since the greater the stability, the longer the emulsion can be safely stored before it is used in vivo. In addition, if the emulsion is very stable, it can be stored without refrigeration; this characteristic is critical for military purposes and in countries where there is little or no refrigeration. Furthermore, a stable emulsion is more predictable from a medical standpoint compared to an emulsion which tends to deteriorate with time. Normally, after administration to an animal, and thus exposure to body temperatures, the internal phase of the emulsion may convert to larger globules. Much remains to be learned about the factors working for and against the emulsion stability in the blood stream and tissues of mammals. While it seems reasonable to suppose that factors which would make for an in vitro stability also make for in vivo stability, there are also special considerations involved in promoting in vivo stability of foreign particles such as perfluorochemical particles. All of the above points to the need for improvements in oxygen transport agents for artificial bloods.

The need for suitable oxygen transport agents is particularly acute at the present time due to the widespread reporting and publicity on acquired immune deficiency syndrome (AIDS). The acquired immune deficiency syndrome virus is also known as HTLV-III. There is no known cure for acquired immune deficiency syndrome which destroys the body's ability to fight cancer and even minor infections. The implication of natural human blood transfusions as an important vector in the propagation of acquired immune deficiency syndrome has magnified the need for an alternative blood replacement fluid. The fact that an HTLV-III blood test has been developed to screen blood donated to blood banks has not decreased the need for the discovery of suitable oxygen transport agents.

Triethylenediamine (1,4-diazabicyclo-[2,2,2]-octane) is a compound which was first reported by Otto Hromatka "Uber das Triethylendiamin (Bicyclo-[2.2.2]-diaza-1.4-octan)" in *Berichte der Deutchen Chemischen Gesellschaft*, 75:1303–1310 (1942) and Otto Hromatka and Eva Engel "Uber das Triethylendiamin (Bicyclo [2.2.2]-1.4-diaza-octan), II. Mitteilung" in *Berichte der Deutchen Chemischen Gesellschaft*, 76:712–722 (1943) as a reaction product of diethanolamine hydrochloride and sodium hydroxide.

As indicated in the *Journal of Chemical and Engineering Data*, Vol. 4, no. 4 (1959) pp. 334–335, triethylenediamine exhibits certain unusual properties which are due to its bicyclic or "cage" structure. The most outstanding properties, such as high melting point and complexing ability, arise from the molecular symmetry and the lack of steric hinderance for both tertiary nitrogen atoms. Triethylenediamine has found a special commercial application as a catalyst in polyurethane foam manufacture. In this application, triethylenediamine's ability to catalyze reactions between isocyanates and hydroxy compounds with great rapidity and yet with a desired balance between rate of foaming and chain growth, is outstanding. Houdry Process Corporation, Linwood, Pa., commercialized triethylenediamine under the name of DABCO ® as a catalyst for the preparation of urethanes following U.S. Pat. No. 2,939,851. It determined that the combination of low basicity with a high vaporization and condensation coefficient which are common to symmetrical cage compounds, promote quick curing of urethane foams which is essential to fast mold release. This cage structure may be beneficial in other applications.

In U.S. Pat. No. 3,335,143, Erner described the fluorination of triethylenediamine by electrolysis of a hydrogen fluoride solution of triethylenediamine in perfluorohexane using a nickel Simon's cell to obtain perfluorotriethylenediamine.

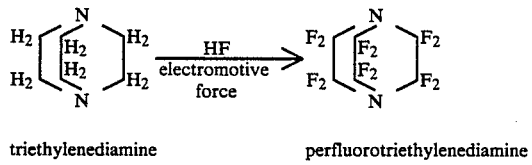

triethylenediamine    perfluorotriethylenediamine

As used herein, perfluorotriethylenediamine indicates that all of the replaceable hydrogen atoms in triethylenediamine have been replaced by fluorine atoms. Perfluorotriethylenediamine is a solid with a melting point above 120° C., which, like its parent triethylenediamine, sublimes rapidly upon heating. Perfluorinated triethylenediamine can also be prepared from triethylenediamine by direct fluorination using elemental fluorine as a minor constituent of an inert gas such as argon.

OBJECTS OF THE INVENTION

Accordingly, a major object of the present invention is to provide novel oxygen transport agents for use in artificial blood compositions.

Another object of the present invention is to provide a novel therapeutical fluorocarbon emulsion preparation having oxygen-carrying ability.

Yet another object of the present invention is to provide a process for preparing novel oxygen transport agents for use in artificial blood compositions.

Other objects and advantages of the present invention will be apparent from the following description.

SUMMARY OF THE INVENTION

Surprisingly, the present inventor has now found that certain highly fluorinated triethylenediamine (1,4-diazabicyclo-2,2,2-octane) compounds are useful as oxygen transport agents in artificial bloods and perfusion fluids. These compounds are preferably perfluorotriethylenediamine, undecafluorotriethylenediamine and decafluorotriethylenediamine and are prepared as emulsions. The emulsions have excellent stability and undergo rapid biological elimination due to their low molecular weight.

The present invention also relates to a novel method for the indirect fluorination of triethylenediamine using a fluoride compound selected from cobalt trifluoride, manganese fluoride, silver fluoride and antimony fluoride. Advantageously, a substantial yet not complete number of the hydrogens on the triethylenediamine compound are replaced with fluorine atoms.

DETAILED DESCRIPTION OF THE INVENTION

The highly fluorinated triethylenediamine compounds of the present invention include perfluorinated triethylenediamine, undecafluorotriethylenediamine and decafluorotriethylenediamine. Other highly fluorinated triethylenediamine compounds may also be useful in small amounts in the preparation of the blood substitute emulsions of the present invention. However, it is generally believed that the lesser the degree of fluorination of the hydrocarbons, the greater the chance of toxicity.

The preferred compound as an oxygen transport agent is the novel compound undecatrifuloroethylenediamine

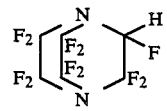

There is only one d,l-optical isomer of undecafluorotriethylenediamine since all of the carbon atoms are equivalent due to symmetry.

The other novel compound of the present invention is decafluorotriethylenedaimine which may appear as one of seven different isomers. The ethylenediamine bicyclic ring structure is generally numbered as follows:

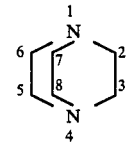

The seven possible positional isomers for decafluorotriethylenediamine include 2,2-(gem), 2,3-(cis and trans), 2,5-(cis and trans) and 2,6-(cis and trans). No particular positional isomer is preferred within this group.

Any of the above-described fluorinated triethylenediamine compounds may be useful as oxygen transport agents in the artificial blood compositions of the present invention. If perfluorotriethylenediamine alone is used in the aqueous artificial blood composition, a colloidal dispersion would likely result. Preferably, undecafluorotriethylenediamine either alone or in combination with perfluorotriethylenediamine and/or decafluorotriethylenediamine is used. Both undecafluorotriethylenediamine and decafluorotriethylenediamine are liquids at ambient temperature. If perfluorotriethylenediamine is present along with undecafluorotriethylenediamine and/or decafluorotriethylenediamine, the perfluorotriethylenediamine is usually soluble in the less fluorinated triethylenediamine compounds, thus making the entire fluorinated triethylenediamine mixture a liquid.

An oxygen transport agent for purposes of the present invention describes a compound which is able to dissolve oxygen and carbon dioxide and thus assist in the transport of oxygen and carbon dioxide through the vascular system of an organism. Oxygen transport agents are useful as perfusion media for body organs as well. Thus, their utility is not limited to replacing blood loss in an organism. An effective oxygen transporting amount of an oxygen transport agent is thus an amount of transport agent capable of transporting oxygen. The present invention claims an artificial blood comprising a physiologically acceptable, stable, essentially homogeneous formulation of an effective oxygen transporting amount of highly fluorinated triethylenediamine dispersed in water, said highly fluorinated triethylenediamine comprising perfluorotriethylenediamine, undecafluorotriethylenediamine, decafluorotriethylenediamine, or any combination thereof. The artificial blood may be emulsified in water and may include the use of an emulsifying agent. The present application also claims a method for replacing blood loss in a mammal, said method comprising administering a physiologically acceptable, stable, essentially homogeneous formulation of an effective amount of an oxygen transporting amount of highly fluorinated triethylenediamine emulsified in water, said highly fluorinated triethylenediamine comprising perfluorotriethylenediamine, undecafluorotriethylenediamine, decafluorotriethylenediamine or any combination thereof. The homogeneous formulation may be emulsified using a copolymer of propylene oxide and ethylene oxide.

The fluorinated triethylenediamine compounds of the present invention can dissolve large amounts of oxygen and carbon dioxide. The gas, i.e., oxygen or carbon dioxide, is chemadsorbed onto the fluorinated triethylenediamine compound. Van der Waal forces maintain the gas and fluorinated compound in close association.

Fluorocarbons are usually immiscible with blood. If directly injected into the body, fluorocarbons will generally coalesce into globules which could clog blood vessels. To prevent this, fluorocarbons used in artificial blood are normally mixed with water to form an emulsion. The liquid fluorinated triethylenediamine compounds when placed in an aqueous system form an emulsion. The emulsion is preferably compatible with the density of blood. As used herein, an emulsion comprises a mixture of two immiscible liquids which also contains an emulsifying agent.

The particles making up the internal phase (dispersed phase) of the emulsion consist of globules of fluorinated triethylenediamine which are immiscible with the aqueous, external phase (dispersion medium).

The fluorinated triethylenediamine compounds can form, for example, an aqueous emulsion containing about 5 to about 75% (W/V), preferably about 10 to about 40% (W/V), of the fluorinated triethylenediamine compounds to be used as oxygen barriers or oxygen transport agents in artificial blood or in infusion fluid. The concentration of fluorinated triethylenediamine compound may depart slightly from these limits. However, emulsions containing substantially greater than 75% (W/V) fluorinated triethylenediamine would be too viscous and too dense to be useful in artificial blood. The viscosity of the fluorinated triethylenediamine emulsion is preferably close to the viscosity of human blood. Emulsions containing substantially less than 15% (W/V), would be so dilute that too much emulsion would be required to provide good oxygen transport.

The symbol "% (W/V)" referred to herein indicates the amount of the fluorinated triethylenediamine by weight (gram) based on 100 milliliter of the resulting emulsion.

On preparing the emulsion an emulsifying agent is used. In general, an emulsifying agent is a compound which prevents droplets or globules in an emulsion from coalescing into larger droplets or globules. Usually, a polymeric nonionic surfactant, a phospholipid and the like are employed each alone or in combination as an emulsifying agent. Possible emulsifying agents include, for example, a fatty acid having 8-22 carbon atoms, particularly 14-20 carbon atoms, or a physiologically acceptable salt thereof (e.g. alkali metal salts such as sodium salt, potassium salt, etc., monoglycerides thereof). Examples of the above fatty acid include caprylic acid, capric acid, lauric acid, myristic acid, palmitic acid, stearic acid, behenic acid, palmitoleic acid, oleic acid, linoleic acid, arachidonic acid, sodium or potassium salts thereof, their glycerides, etc. Other emulsifying agents include dextran, albumins, fluorinated amine oxides, nonylphenol polyethylene glycols or fluorinated alcohols.

The polymeric nonionic surfactant used herein may be that having a molecular weight of 2,000-20,000, and examples thereof include polyoxyethylene-polyoxypropylene copolymers, polyoxyethylene fatty acid esters, polyoxyethylene castor oil derivatives, etc. Examples of phospholipids include vitelline phospholipid, soybean phospholipid, etc.

The preferred emulsifying agent is Pluronic ® F-68, a high molecular weight polyoxyethylenepolyoxypropylene copolymer. This is the emulsifier used in Fluosol ®-DA, a composition prepared according to U.S. Pat. No. 4,252,827, which is a product of Green Cross Corporation of Japan. Investigators have found that Pluronic ® F-68 inhibits blood coagulation and aggregation of platelets.

An artificial blood substitute must provide proper osmotic and oncotic pressures and reasonable pH control, as well as oxygen and carbon dioxide transport. Thus, as the medium for the emulsion, a physiologically acceptable aqueous solution is generally employed. Oftentimes, physiological saline and lactic acid added Ringer's solutions are used. The typical salts found in physiological salt solutions include potassium chloride, magnesium chloride, sodium chloride, calcium chloride and the like. The pH is preferably within the range of normal physiological pH, more preferably within the range of about 7.2 to about 7.4.

If necessary, there may be further added an isotonizing amount of an isotonizing agent such as glycerol to isotonize the emulsion and a plasma expander such as hydroxyethylstarch, dextran, etc. to regulate the colloid osmotic pressure of the emulsion.

The aqueous dispersions of the present invention are prepared by any mixing technique which will provide a uniform blend of the ingredients. The components may be mixed in any order. The emulsion can be prepared by mixing the above-mentioned ingredients and homogenizing the mixture by means of, for example, a high-pressure jet type homogenizer until the particle diameters fall within the desired particle size range. A suggested particle size range is within about 10 0.005 to about 0.5 μm, preferably about 0.5 to about 0.3 μm. Emulsions with controllable droplet or particle sizes can also be created by conventional high-shear emulsifiers, e.g., the Manton-Gaulin homogenizer.

One preparative mixing technique involves mixing the emulsifier with water under suitable agitation followed by introduction of the fluorinated triethylenediamine. Since the fluorinated triethylenediamine is extremely hydrophobic, high energy mixing is generally employed, such as homogenization or sonic energy. One such device is the Sonicator ®, model 350, available from Heat-Systems Ultrasonics Inc. This device has a maximum power output of 350 watts controllable on settings of 1-10. Because the dispersion will rapidly heat up during blending in the Sonicator, it is preferred to blend over several mixing cycles separated by cooling periods.

When the fluorinated triethylenediamine emulsion preparation of the present invention is employed, as a transfusion for oxygen transport, it is generally administered by intravenous injection, and the dosage for a human adult is generally about 50 to 3,000 milliliters per dose.

Other fluorocarbons in addition to fluorinated triethylenediamine compounds may be present as additional oxygen transport agents in the artificial blood emulsion. However, not all fluorocarbons are useful in artificial blood preparations. Fluorocarbons sometimes tend to accumulate in body tissues, notably the liver and spleen. Some fluorocarbons are emulsified only with difficulty. Perfluorodecalin has been found to be the best perfluorocarbon in terms of speed of elimination from the liver and spleen. Perfluorotripropylamine is more easily emulsified than perfluorodecalin but has a considerably slower rate of elimination from the liver and spleen. Other perfluoro compounds which have been used are perfluoromethyldecalin, perfluorotributylamine, perfluoro-1,3-dimethylcyclohexane, perfluorinated bis-neopentyl ether, perfluorinated bis-isopropyl ether, perfluorinated bis-isobutyl ether, perfluorinated bisisopentyl ether, perfluorinated bis-tertiarybutyl ether and the like.

Perfluorocyclocarbons may also be present in the emulsions of the present invention. The term "perfluorocyclocarbon" means a cyclic compound of carbon, whereas the term "substituted derivatives thereof" characterizes substituted perfluorocyclocarbons with acyclic or alkyl side chains, preferably lower alkyl side chains. It should also be noted that the term "perfluorocyclocarbon" denotes substitution of all hydrogen atoms attached to the carbon atom chain or ring and any carbon side groups with fluorine. It is conceivable in the manufacture of such compounds that minor amounts of substantially fluorinated derivatives may be mixed with completely fluorinated compounds. This is permissible providing the lack of complete replacement of all hydrogens does not affect the essential characteristics of the liquid perfluorocarbons of this invention, particularly when the active hydrogens critically enhance the toxicity of the compounds when they are employed as oxygen transport agents in animals. Among the perfluorocyclocarbons which may be employed are perfluorobicyclo[4.3.0]nonane, perfluorotrimethylcyclohexane, perfluoroisopropylcyclohexane, perfluoroendotetrahydrodicyclopentadiene, perfluoroadamantane, perfluoroexotetrahydrodicyclopentadiene, perfluorobicyclo[5.3.0]decane, perfluorotetramethylcyclohexane, perfluoro-1-methyl-4-isopropylcyclohexane, perfluoro-n-butylcyclohexane, perfluorodimethylbicyclo[3.3.1]nonane, perfluoro-1-methyl adamantane, perfluoro-1-methyl-4-t-butylcyclohexane, perfluorodecahydroacenaphthene, perfluorotrimethylbicyclo[3.3.1]nonane, perfluoro-n-undecane, perfluorotetradecahydrophenanthrene, perfluoro-1,3,5,7-tetramethyladamantane, perfluorododecahydrofluorene, perfluoro-1,3-dimethyl adamantane, perfluoro-n-octylcyclohexane, perfluoro-7-methyl bicyclo[4.3.0]nonane, perfluoro-p-diisopropylcyclohexane, perfluoro-m-diisopropylcyclohexane, perfluoroazabicyclodecane, and perfluorooctahydroquinolizine.

The ability of the emulsions of the present invention to maintain low particle size over long periods of time at room temperature indicates exceptional stability, making them valuable as blood substitutes and therapeutic agents. The improved emulsion stability is likely due to the high nitrogen content of the fluorinated triethylenediamine compounds. This allows long shelf-life stability at ambient temperature. There is no need to refrigerate the emulsion of the present invention.

The fluorinated triethylenediamine compounds of the present invention are also particularly advantageous due to their rapid biological elimination. It is believed that the half-life of these compounds is about seven days. The short half-life is probably due to the low molecular weight of these compounds as well as the cage structure of the triethylenediamine. The rapid rate of vaporization and condensation assist in the rapid elimination of the fluorinated triethylenediamine compounds from the body by allowing the compounds to easily pass through the lungs of a mammal. The low vaporization temperature of the fluorinated triethylenediamine compounds are also advantageous because this acts to prevent the formation of emboli.

The highly fluorinated triethylenediamine compounds of the present invention can be prepared by the indirect fluorination of triethylenediamine by passing the triethylenediamine over a fluoride compound selected from the group consisting of cobalt trifluoride, manganese fluoride, silver fluoride, and antimony fluoride. Cobalt trifluoride is preferred. A sufficient amount of fluoride compound is used to obtain the desired distribution of fluorinated triethylenediamine product depending on the reaction conditions selected. The amount of fluoride compound used is generally in the range of about 20 to about 40 equivalents of fluoride compound per equivalent of triethylenediamine.

Generally, the triethylenediamine is mixed with an inert gas and then moisture is removed. The triethylenediamine inert gas mixture is then passed over or contacted with one of the fluoride compounds described above. The reaction temperature is generally within the range of about 80° C. to about 350° C., preferably 100° C. to 300° C. The reaction pressure is generally atmospheric pressure, however, pressures ranging from 18 mm Hg to about 300 psig are suitable in the practice of the present invention. Reaction time varies and depends on reactants and conditions selected. Generally, a reaction time of about five minutes to four hours is suitable depending on the rate of flow of the triethylenediamine over the fluorinated compound.

The process of the present invention is particularly advantageous since it does not fully fluorinate the triethylenediamine as do the prior art processes. In particular, Barbour et al "The Fluorination of Hydrocarbons with Cobalt Trifluoride," *J. Appl. Chem.* 2 (1952) pages 127–133 teaches the complete fluorination of hydrocarbons using cobalt trifluoride. Only Applicant's novel process produces not only perfluorotriethylenediamine but also substantial amounts of undecafluorotriethylenediamine and decafluorotriethylenediamine. This entire reaction product is particularly useful in the artificial blood substitute of the present invention.

In order to further illustrate the present invention and the advantages thereof, the following specific examples are given, it being understood that same are intended only as illustrative and in nowise limitative.

EXAMPLE 1

Preparation of Fluorinated Triethylenediamine

A vaporized mixture of five (5) grams of triethylenediamine in high purity argon gas was passed over Linde molecular sieves to remove moisture. The vaporized mixture of triethylenediamine was passed through a 8 inch by 10 feet coil of copper tubing which was packed with a mixture of 8 inch copper helices (90% void space) and powdered cobalt trifluoride (CoF$_3$) which was placed in a 4-liter beaker and surrounded by a solution of ethylene glycol and propylene glycol as a heat exchange medium and placed on a heated magnetic stirrer.

The initial reactor bath temperature was 149° C. but was gradually raised to 157° C. The reactor bath temperature was then raised to 193° C. over two hours and finally to 200° C. over 15 minutes.

The effluent argon gas containing fluorinated triethylenediamine and hydrogen fluoride was passed into a second 8 inch×10 feet copper tubing coil immersed in ethylene glycopropylene glycol dry ice mixture.

The second copper coil trap was then permitted to warm to room temperature over twenty-four hours, while separating hydrogen fluoride through an efficient copper reflux condenser. The trap products consisted of a mobile colorless liquid with a slight yellowish tint.

A sample of the trap products was passed through a gas chromatograph for analysis. A major peak (68%) having a parent peak in a mass spectrometer of 328, a secondary peak (24%) having a parent peak of 310, and a series of smaller peaks having parent masses of 292 were found.

The mass of 328 corresponds to perfluorotriethylenediamine, the mass of 310 corresponds to undecafluorotriethylenediamine and the peaks of mass 292 correspond to decafluorotriethylenediamine.

A fraction of the trap products was used to determine molecular weight by boiling point elevation of perfluoro-1,3-dimethylcyclohexane (b.p.$_{760}$101°-2° C.). A corrected value for barometric pressure gave a molecular weight of 321.

EXAMPLE 2

Preparation of Fluorinated Triethylenediamine Emulsion

Approximately 2 cc of the trap contents from Example 1 dissolved in 10 cc of perfluorodecalin and 5 grams of Pluronic -F68 emulsifier were added. Deionized water through a Millipore nylon 66 filter of 2 microns was added and the total volume was brought to 50 milliliters. The mixture in a calibrated water-cooled glass container, was subjected to emulsification with a VC 400, 500 watts, 28 kHz Vibra-Cell ultrasonic emulsifier (Sonics and Materials, Inc., Danbury, Conn.) intermittently until a stable nearly clear emulsion was obtained. The emulsified fluorinated triethylenediamine was chromatographed over ion exchange columns of sulfonated polystyrene to remove basic amine contaminants and IRA-400 Amberlite (—OH$^-$) to remove hydrogen fluoride formed by emulsification.

A twenty cc sample of the purified fluorinated triethylenediamine/perfluorodecalin emulsion was compared at intervals of one week and two weeks with a control emulsion of perfluorodecalin. The fluorinated triethylenediamine/perfluorodecalin showed improved stability, that is, it was likely for the dispersed phase globules to increase in size.

EXAMPLE 3

Preparation of Fluorinated Triethylenediamine

Using a stirred metal reactor as described by Barbour et al in "The Fluorination of Hydrocarbons With Cobalt Trifluoride", *J. Appl. Chem.*, 2 (1952) pages 127-133, 200 grams of triethylenediamine in a solution of perfluoro-1,3-dimethylcyclohexane were passed through the heated agitated reactor through programmed zones of temperature from 120° C. to 290° C. The product was collected in copper dry ice traps. After removal of hydrogen fluoride and fractional distillation through a 15 theoretical plate column at reduced pressure, a fraction higher boiling than the perfluoro-1,3-dimethylcyclohexane was obtained. This fraction was a liquid of a slight yellow tint. Samples vaporized readily when molecular sieve dried nitrogen was sparged through them.

Molecular weight determination by boiling point elevation of perfluoro-1,3-dimethylcyclohexane gave a barometrically corrected value of 319.

EXAMPLE 4

Preparation of Fluorinated Triethylenediamine Emulsion

To 10 milliliters of the fraction of the fluorination product of triethylenediamine of Example 3 were added 5 grams of Pluronic ® F-68 emulsifier, and the total volume increased to 50 milliliters with deionized-micro filtered water. This material was ultrasonified with a VC 250, 250 watt, 20 kHz variable power output Vibra-Cell unit (Sonics and Materials, Inc.) until a stable nearly clear emulsion resulted. The emulsion was maintained at 10°-15° C. by efficient ice cooling to avoid loss of the fluorinated triethylenediamine.

30 milliliters of the emulsion was agitated in a glass tube containing a nitrogen sparge inlet. Weight loss of the emulsion at 25° C. over three hours was 0.23 gram/hour. By comparison a comparable control emulsion of perfluorotributylamine had a weight loss of 0.04 gram/hour.

EXAMPLE 5

Preparation of Fluorinated Triethylenediamine Emulsion

An emulsion was produced as in Example 4 using 2 milliliters of fluorinated triethylenediamine and 8 milliliters of perfluorodecalin.

This emulsion was quite stable but inferior to that of Example 2.

EXAMPLE 6

Preparation of Fluorinated Triethylenediamine Emulsion

An emulsion was produced as in Example 4 using 2 milliliters of fluorinated triethylenediamine, 4 milliliters of perfluorotributylamine and 4 milliliters of perfluorodecalin.

EXAMPLE 7

Preparation of Fluorinated Triethylenediamine Emulsion

An emulsion was produced as in Example 4, and placed in a 125 milliliter agitated spherical flash in a closed system with access through a 9 milliliter glass tube to a calibrated burrette containing oxygen gas at atmospheric pressure. After 45 minutes equilibration, absorbed oxygen from the burrette was measured. Results were compared to those obtained with a comparable emulsion of perfluorotributylamine. The fluorinated triethylenediamine emulsion, in duplicate tests had an average of 93% of the oxygen absorbing capacity of the perfluorotributylamine emulsion.

EXAMPLE 8

Preparation of Fluorinated Triethylenediamine Emulsion with Physiological Salt Solution An emulsion of 10 milliliters of a fraction of the fluorination product of triethylenediamine obtained in Example 4 was prepared and brought to a volume of 50 milliliters. The emulsion was passed over ion exchange beds to remove any basic amines and hydrogen fluoride formed during ultrasonification.

To this emulsion was added with stirring on a magnetic stirrer, 1.5 grams hydroxyethyl starch, 0.05 grams glucose, 16 milligrams potassium chloride, 3.5 milligrams magnesium chloride, 4.8 milligrams monosodium phosphate, 27 milligrams sodium chloride, 9 milligrams calcium chloride, and the pH was adjusted to 7.45 with sodium carbonate. Stirring was continued for 30 minutes after the additives dissolved. The final emulsion was again filtered through a Millipore filter (0.2 micron).

While this invention has been described in terms of various preferred embodiments, the skilled artisan will appreciate that various modifications, substitutions, omissions, and changes may be made without departing from the scope thereof. Accordingly, it is intended that the scope of the present invention be limited solely by the scope of the following claims.

I claim:

1. An artificial blood comprising a physiologically acceptable, stable, essentially homogeneous formulation of an effective oxygen-transporting amount of highly fluorinated triethylenediamine dispersed in water, said highly fluorinated triethylenediamine comprising perfluorotriethylenediamine, undecafluorotriethylenediamine or decafluorotriethylenediamine, or any combination thereof.

2. An artificial blood as defined by claim 1, wherein said highly fluorinated triethylenediamine is emulsified in water.

3. An artificial blood as defined by claim 2, further comprising an emulsifying agent.

4. An artificial blood as defined by claim 3, wherein said highly fluorinated triethylenediamine comprises perfluorotriethylenediamine.

5. An artificial blood as defined by claim 3, wherein said highly fluorinated triethylenediamine comprises undecafluorotriethylenediamine.

6. An artificial blood as defined by claim 3, wherein said highly fluorinated triethylenediamine comprises decafluorotriethylenediamine.

7. An artificial blood as defined by claim 3, wherein said emulsifying agent is a copolymer of propylene oxide and ethylene oxide.

8. An artificial blood as defined by claim 3, wherein said formulation is isotonic.

9. A method for replacing blood loss in a mammal, said method comprising intravenously administering a physiologically acceptable, stable, essentially homogeneous formulation of an effective oxygen transporting amount of highly fluorinated triethylenediamine emulsified in water, said highly fluorinated triethylenediamine comprising perfluorotriethylenediamine, undecafluorotriethylenediamine, decafluorotriethylenediamine or any combination thereof.

10. A method for replacing blood loss in a mammal as defined by claim 9, wherein said homogeneous formulation is emulsified with a copolymer of propylene oxide and ethylene oxide.

11. An artificial blood as defined by claim 1, wherein said highly fluorinated triethylenediamine comprises about 5 to about 75% (W/V) of the artificial blood.

12. An artificial blood as defined by claim 11, wherein said highly fluorinated triethylenediamine comprises about 10 to about 40% (W/V) of the artificial blood.

13. A stable, essentially homogeneous dispersion comprising an effective oxygen transporting amount of highly fluorinated triethylenediamine in water, said highly fluorinated triethylenediamine comprising perfluorotriethylenediamine, undecafluorotriethylenediamine or decafluorotriethylenediamine, or any combination thereof.

14. A stable, essentially homegeneous dispersion as defined by claim 13, wherein said highly fluorinated triethylenediamine comprises perfluorotriethylenediamine.

15. A stable, essentially homogeneous emulsion comprising an effective oxygen transporting amount of highly fluorinated triethylenediamine in water, said highly fluorinated triethylenediamine comprising perfluorotriethylenediamine undecafluorotriethylenediamine, decafluorotriethylenediamine or any combination thereof.

16. A stable, essentially homogeneous emulsion as defined by claim 15, wherein said highly fluorinated triethylenediamine comprises perfluorotriethylenediamine.

17. A stable emulsion in a physiologically acceptable aqueous medium of highly fluorinated triethylenediamine having a particle size of about 0.005 to about 0.5 μm which comprises about 5 to about 75% (W/V) of the emulsion and an effective surfactant amount of a polymeric nonionic surfactant which is a copolymer of propylene oxide and ethylene oxide having a molecular weight of 2,000 to 20,000, said highly fluorinated triethylenediamine comprising perfluorotriethylenediamine, undecafluorotriethylenediamine, decafluorotriethylenediamine or any combination thereof.

* * * * *